(12) United States Patent
Michot et al.

(10) Patent No.: US 8,512,899 B2
(45) Date of Patent: *Aug. 20, 2013

(54) POLYMERS OBTAINED FROM MONOMERS ALLOWING A SEQUENTIAL POLYMERIZATION, AND THEIR USE FOR PREPARING IONIC CONDUCTORS

(75) Inventors: Christophe Michot, Grenoble (FR); Alain Vallee, Varennes (CA); Paul-Etienne Harvey, Saint-Hubert (CA); Michel Gauthier, LaPrairie (CA); Michel Armand, Montreal (CA)

(73) Assignee: Hydro-Quebec (CA)

( * ) Notice: Subject to any disclaimer, the term of this patent is extended or adjusted under 35 U.S.C. 154(b) by 59 days.

This patent is subject to a terminal disclaimer.

(21) Appl. No.: 12/118,483

(22) Filed: May 9, 2008

(65) Prior Publication Data

US 2008/0213661 A1  Sep. 4, 2008

Related U.S. Application Data

(60) Continuation of application No. 10/860,017, filed on Jun. 4, 2004, now abandoned, which is a continuation of application No. 10/314,325, filed on Dec. 9, 2002, now abandoned, which is a continuation of application No. 10/139,320, filed on May 7, 2002, now Pat. No. 6,492,449, and a division of application No. 09/337,251, filed on Jun. 22, 1999, now abandoned.

(30) Foreign Application Priority Data

Jun. 25, 1998 (CA) ..................... 2242017
Jul. 10, 1998 (CA) ..................... 2243103

(51) Int. Cl.
*H01M 10/40* (2006.01)
*H01M 6/18* (2006.01)

(52) U.S. Cl.
USPC ........... 429/311; 429/304; 429/306; 429/309; 429/310

(58) Field of Classification Search
None
See application file for complete search history.

(56) References Cited

U.S. PATENT DOCUMENTS

| | | | |
|---|---|---|---|
| 4,886,716 A | 12/1989 | Roggero et al. | |
| 5,064,548 A | 11/1991 | Roggero et al. | |
| 5,146,005 A | 9/1992 | Weitemeyer et al. | |
| 5,162,174 A | 11/1992 | Andrei et al. | |
| 5,173,205 A | 12/1992 | Marchese et al. | |
| 5,264,307 A | 11/1993 | Andrei et al. | |
| 5,411,819 A | 5/1995 | Marchese et al. | |
| 5,501,920 A | 3/1996 | Andrei et al. | |
| 5,523,180 A | 6/1996 | Armand et al. | |
| 5,605,941 A | 2/1997 | Steinmann et al. | |
| 5,665,841 A | 9/1997 | Kim et al. | |
| 5,696,224 A | 12/1997 | Benrabah et al. | |
| 5,700,880 A | 12/1997 | Sanchez et al. | |
| 6,030,421 A * | 2/2000 | Gauthier et al. | 29/623.1 |
| 6,063,522 A * | 5/2000 | Hamrock et al. | 429/200 |
| 6,239,204 B1 | 5/2001 | Miura et al. | |

FOREIGN PATENT DOCUMENTS

| | | |
|---|---|---|
| CA | 2058104 A1 | 6/1992 |
| EP | 421230 A2 | 4/1991 |
| EP | 657485 A1 | 6/1995 |
| GB | 836046 A | 6/1960 |
| GB | 2292945 A | 3/1996 |
| JP | 05-182512 A | 7/1993 |
| WO | 95/15991 A1 | 6/1995 |
| WO | 96/08051 A1 | 3/1996 |
| WO | 97/42251 A1 | 11/1997 |

OTHER PUBLICATIONS

P.L. Dhinghra & R. D. Verma, "Chemistry of Bis(sulphuryl fluoride)amine: Part IV—Complexes of $Me_4NN(SO_2F)_2$ with Titanium(IV), Vanadium(III), Manganese(II), Iron(II & III), Cobalt(II), Nickel(II), & Copper(II) Chlorides", Journal of Indian Chemistry, vol. 26A, Feb. 1987, pp. 139-141.

* cited by examiner

*Primary Examiner* — Ula C Ruddock
*Assistant Examiner* — Tony Chuo
(74) *Attorney, Agent, or Firm* — Katten Muchin Rosenman LLP

(57) ABSTRACT

The present invention concerns polymers obtained by anionic initiation and bearing functions that can be activated by cationic initiations that are not reactive in the presence of anionic polymerization initiators. The presence of such cationic initiation functions allow an efficient cross-linking of the polymer after molding, particularly in the form of a thin film. It is thus possible to obtain polymers with well-defined properties in terms of molecular weight and cross-linking density. The polymers of the present invention are capable of dissolving ionic compounds inducing a conductivity for the preparation of solid electrolytes.

7 Claims, No Drawings

POLYMERS OBTAINED FROM MONOMERS ALLOWING A SEQUENTIAL POLYMERIZATION, AND THEIR USE FOR PREPARING IONIC CONDUCTORS

RELATED APPLICATION DATA

This application is a continuation of U.S. patent application Ser. No. 10/860,017, filed Jun. 4, 2004, now abandoned, which is a continuation of U.S. patent application Ser. No. 10/314,325, filed on Dec. 9, 2002, now abandoned, which is a continuation of U.S. patent application Ser. No. 10/139,320, filed May 7, 2002, now U.S. Pat. No. 6,492,449, which is a divisional of U.S. patent application Ser. No. 09/337,251, filed on Jun. 22, 1999, now abandoned, the contents of which are incorporated by reference in their entirety.

FIELD OF THE INVENTION

The present invention concerns polymers obtained by anionic initiation and bearing functions that can be activated by cationic initiations that are not reactive in the presence of anionic polymerization initiators. The presence of such cationic initiation functions allow an efficient cross-linking of the polymer after moulding, particularly in the form of a thin film. It is thus possible to obtain polymers with well-defined properties in terms of molecular weight and cross-linking density.

BACKGROUND OF THE INVENTION

Three types of polymerization mechanisms are mainly known, i.e. anionic, cationic and radicalar. Generally, monomers bearing double bond-type functions conjugated or activated and allowing propagation of radicalar species are mostly used. It is however difficult to control the molecular weights of the polymer, especially because the radicals are inactivated by oxygen. Recently, monomers bearing vinyl ether-type functions $CH_2=CHO$— with a high cationic polymerization reactivity have been commercialized. Cationic polymerization, though very rapid, hardly leads to high molecular weights mainly because of the fact that the carbocations allowing the propagation of the polymerization are sensitive to water or other nucleophilic species present in the reaction medium.

The compositions mainly used for making films, varnishes or inks generally combine epoxide-type monomers with monomers bearing one or more vinyl ether functions, and are polymerized with cationic catalysts. Because the polymerization of epoxides and the polymerization of vinyl ethers are propagating at very different speeds, the macromolecular solids obtained are usually made of interpenetrated networks corresponding to each type of monomers. The polymerization degree and cross-linking density of such systems are thus hardly controllable. The mechanical properties are more dependent on the rigidity of the chains or the presence of OH functions providing strong hydrogen bonds. These compositions, particularly those to which glycol or triol vinyl diether are added, allow nevertheless the minimization of volatile solvent consumption because of the low viscosity of the corresponding monomers (so-called "reactive diluents"). In that respect, vinyl ethers have a low toxicity.

The "reactive diluent" notion is also used with monomer mixtures of the acrylic type (radicalar) with monomers of the vinyl ether type, in the presence of radicalar initiators added to cationic initiators. It is however as difficult with this procedure to ensure a regular control of the polymerization/cross-linking rate because of the radicalar polymerization sensitivity to oxygen. This problem is particularly true for thin films with a major portion of their surface in contact with air. Polyfunctional monomers containing a vinyl ether function have been described in U.S. Pat. No. 5,605,941. These compounds are used to obtain cross-linked resins having a high glassy transition temperature through a single step process using interpenetrated networks of the (cationic+cationic) or (cationic+radicalar) type.

Anionic polymerization has various advantages in terms of the accurate control of the molecular weight, particularly for a narrow distribution of the weights $M_w/M_n$. This is the method of choice to prepare polymers with a predetermined weight and elaboration of bloc polymers of the type AB, ABA, or branched. However, the initiators and the anionic species allowing the propagation are highly reactive. These species are either organometallics or alkaline metal alkoxides that react with most organic functions borne by the monomers, particularly those that would allow easy cross-linking later, such as functions containing epoxides, alcohols or amines, or double bonds activated with one or more conjugated double bonds, and aromatic nucleus or an electron attracting group like $C=O$, $C\equiv N$. The water or other nucleophile exclusions conditions during the polymerization cause the polymer to be prepared in dedicated units, rather than at the time of use or moulding.

Also known are polymers having ether functions in high concentration, generally between 40 and 100% molar, particularly containing units $—[(CH_2H(R)O]_n—$ wherein $4 \leq n \leq 2 \times 10^4$ and R is H or an alkyl group of 1 to 4 carbon atoms, or a polymerizable group such as the allyloxy-methyl group. The copolymers, in particular those wherein R is mainly H, possess the property of dissolving certain salts, metallic or onium (ammonium, amidinium, guanidinium) to form conductive solid solutions. Lithium salts are particularly useful to form electrolytes that can be used in primary or secondary batteries, supercapacities, or light modulation systems, also called "electrochromic". The environment in which these materials work, in particular in contact with highly reductive elements, such as metallic lithium, alloys thereof or solid solutions thereof in the various forms of carbon, like graphite or cokes, requires an increased stability of the bonds of the polymer, that are mainly limited to CH and C—O bonds of the ether functions. Because of the low intrinsic conductivity of these materials, they are embodied in thin films having nevertheless good mechanical behaviour. This is obtained either by using high molecular weights, or more conveniently, through a cross-linking process. The latter method, however, has the disadvantage of increasing the glassy transition temperature ($T_g$) of the network, which is the most important parameter to determine the conductivity. Further, the allyloxymethyl functions introducing the functions allowing the cross-linking, in particular with the monomer allyl-glycidyl ether (AGE), that are resistant to the action of catalysts for the anionic polymerization, are not very active for the later formation of cross-linking knots, and it is impossible to control exactly the cross-linking density of the materials containing this monomer. It is difficult to implicate more that 50% of the double bonds during the cross-linking.

Polymers obtained from oligo(ethylene oxide) vinyl ethers have been proposed as solid electrolytes, for example in U.S. Pat. No. 4,886,716, U.S. Pat. No. 5,064,548, U.S. Pat. No. 5,173,205, U.S. Pat. No. 5,264,307, U.S. Pat. No. 5,411,819 and U.S. Pat. No. 5,501,920, and possess acceptable conductive properties. The preparation of the corresponding monomers is however delicate. These materials, before cross-linking, have a low molecular weight, as for most of cationic polymerizations. Indeed, the monomers are highly hygroscopic, and thus difficult to purify. In addition, the mechanical properties of the polymers are poor because of the absence of entanglement, a phenomenon typical to polymers with lateral chains. By using polyfunctional monomers of the vinyl diether-type, it is possible to obtain cross-linked products, but it is however impossible to separate the polymerization step from the cationic cross-linking process, and as a result, there is substantially no control of the process for obtaining the cross-linked polymer.

SUMMARY OF THE INVENTION

In accordance with the present invention, there is now provided a cross-linkable polymer obtained by anionic polymerization initiation followed by cationic cross-linking, the polymer being of general formula:

$$(A)_nQ(Y)_p$$

wherein

Q represents a bond, —CO—, —SO$_2$—, or an organic radical of n+p valence non reactive towards reagents initiating anionic or cationic polymerization, of the type alkyl, alkylaryl, arylalkyl optionally comprising oxa or aza substituents, and comprising from 1 to 30 carbon atoms;

A represents a radical reactive in anionic polymerization;

Y represents a radical reactive in cationic polymerization and non-reactive toward agents initiating anionic polymerization;

n varies between 1 and 3; and p varies between 1 and 6.

In a preferred embodiment, A comprises

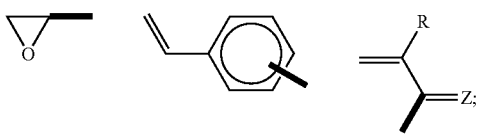

Y comprises

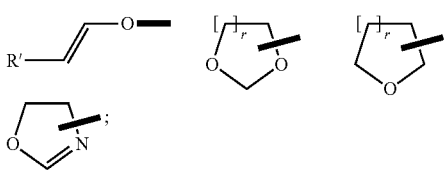

wherein

Z represents O or CH$_2$;

R represents H, an alkyl or oxa-alkyl radical of from 1 to 12 carbon atoms, CN or CH$_2$COOR$^1$ wherein R$^1$ is H or an alkyl or oxa-alkyl radical of 1 to 12 carbon atoms;

R' represents H or an alkyl radical of 1 to 12 carbon atoms; and r varies between 1 and 6.

The polymers of the present invention are capable of dissolving ionic compounds inducing a conductivity, for the preparation of solid electrolytes.

DETAILED DESCRIPTION OF THE INVENTION

The present invention relates to polymers obtained by anionic initiation and bearing functions that can be activated by cationic initiation and allowing an efficient cross-linking of the polymer after moulding, particularly in the form of a thin film. The functions active in cationic polymerization are thus chosen for their stability towards reagents allowing the anionic polymerization. It is therefore possible to obtain polymers with well-defined properties in terms of molecular weight and cross-linking density, by taking advantage of the cumulated benefits of both types of polymerization. The cross-linking is performed efficiently, and totally independently in particular of the action of oxygen.

Also part of the present invention and representing an important aspect thereof, are the polymers obtained by anionic polymerisation and cross-linked cationically, capable of dissolving ionic compounds inducing a conductivity for the preparation of solid electrolytes. As mentioned above, the necessity of being capable of introducing functions allowing the cross-linking without compromising the chemical or electrochemical stability of the system and without a noticeable increase of the glassy transition temperature, is critical. The polymers of the invention meet these criteria because of the selection of the active groups for the cationic polymerization that allow an efficient and controlled cross-linking.

The monomers used for obtaining the polymer according to the invention are defined by the general formula:

$$(A)_nQ(Y)_p$$

wherein

Q represents a bond, —CO—, —SO$_2$—, or an organic radical of n+p valence non reactive towards reagents initiating anionic or cationic polymerization, of the type alkyl, alkylaryl, arylalkyl optionally comprising oxa or aza substituents, and comprising from 1 to 30 carbon atoms;

A represents a radical reactive in anionic polymerizations;

Y represents a radical reactive in cationic polymerization and non-reactive toward agents initiating anionic polymerization;

n varies between 1 and 3; and p varies between 1 and 6.

Preferably, n is 1 except when it is advantageous to dispose directly of a cross-linked material and it is desirable to pursue its cross-linking cationically. When n is 2, two functions borne by the same monomer polymerize together, as for those leading to the formation of cycles without cross-linking. It can also be interesting to mix monomers wherein n=1 to a small fraction, for example, 0.1 to 10%, of a polyfunctional monomer to increase the molecular weight by creating branches compensating the natural end of the chains.

The polymers of the invention are prepared by anionic polymerization and contain monomers as defined above wherein A preferably comprises:

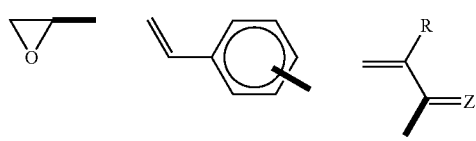

wherein

Z represents O or CH$_2$;

R represents H, an alkyl or oxa-alkyl radical of from 1 to 12 carbon atoms, CN or CH$_2$COOR$^1$ wherein R$^1$ is H or an alkyl or oxa-alkyl radical of 1 to 12 carbon atoms.

In the same monomers, Y preferably comprises

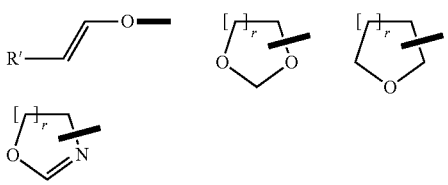

wherein

R' represents H or an alkyl radical of 1 to 12 carbon atoms; and r varies between 1 and 6.

The life span of the cationic species allowing the propagation of the polymerization/cross-linking being particularly long when compared to that of radicalar species, the reaction can carry on after initiation with a cationic polymerization initiator, until complete consumption of the Y groups. In particular, a brief exposure to heat or an actinic radiation is sufficient to initiate the reactive species, and polymerization can continue even in the absence of the activating agent, especially because of the absence of termination reaction caused by the oxygen in the air.

Suitable anionic-type initiators comprise preferably organometallics, amides, alkoxides, strong bases derived from dialkyl-aminophosphines. Preferred organometallics comprise alkyllithium derivatives, such as butyllithium (primary, secondary or tertiary), hexyllithium, and lithium, sodium or potassium derivatives of 1,1'-diphenylethylene, tetraphenylethylene, naphthalene, biphenyle or benzophenone. Preferred amides comprise $NaNH_2$, $Ca(NH_2)_2$, their addition products with epoxydes, dialkylamide derivatives like lithium di-isopropylamide. Preferred alkoxides comprise methoxide, ethoxide, butoxide (primary, secondary, tertiary) or tert-amyloxide derivatives of alkaline metals, alkoxides of linear alcohols of from 8 to 18 carbon atoms, monoalcohol polyethylenes of weight comprised between 400 and 800, alkoxides of polyhydric alcohols, such as glycol, glycerol, oligoethylenes glycol, sorbitol, pentaerythritol, trimethylolpropane, bis-trimethyloldiethylether, bisphenol A and their polyethoxylated derivatives. Preferred strong bases comprise dialkylaminophosphines derivatives such as 1-tert-butyl-4,4,4,-tris[dimethylamino-2,2-bis(trisdimethylamino)-phosphoranylideneamino]-2λ5-4λ5-catenadi(phosphazene), commonly known as "phosphazene base P4-t-bu". Generally, organometallic and dialkylamide derivatives, in particular lithium derivatives, are preferred to initiate the polymerization of the double bonds activated by other conjugated double bond C=C or C=O, such as derivatives of butadiene, styrene, and acrylic or methacrylic acid. For the polymerization of epoxides, alkaline metal derivatives like mono or polyhydroxylic alcohols of sodium and particularly potassium leading to the formation of straight or branched chains, are preferred. Dialkylaminophosphines are reactive for acrylates or epoxides. The activity of the organometallic, amide or alkoxide derivatives can be increased in the presence of molecules susceptible of strongly solvating alkaline ions, for example THF, dialkyl ethers of oligoethylene glycols containing between 2 and 16 carbon atoms and usable as solvents. Peralkyl(polyethyleneimines) of 2 to 8 atoms of nitrogen, particularly tetramethylethylene diamine (TMDA), pentamethyldiethylenediamine, and tris (2-dimethylaminoethylamine) have activating properties particularly interesting.

The polymers of the invention obtained after the initial anionic polymerization are cross-linked by a cationic process using the monomer groups designed for that purpose. Generally, the catalysts allowing the propagation of the reaction of polymerization/cross-linking are Lewis or Brønsted acids. Most reactive Lewis acids comprise derivatives of aluminum, boron, zinc of the type $B(Hal)_3$, $Al(Hal)_3$, $Zn(Hal)_2$ wherein Hal is a halogen or pseudohalogen, or an alkyl, aryl or zinc halides group. Brønsted acids are on the other hand susceptible of giving a cation with a surface charge higher than $3 \times 10^{-19}$ coulombs/Å$^2$. Other cations that correspond to the charge criteria comprise, without restriction, $Li^+$, $Mg^{2+}$, $Ca^{2+}$, $Zn^{2+}$, $Sn^{2+}$, $Al^{3+}$ etc. Most reactive derivatives correspond to strong acids and anions $X^-$ weakly basic or weakly nucleophilic. Example of such anions are $AlCl_4^-$, $BF_4^-$, $PF_6^-$, $AsF_6^-$, $SbF_6^-$, $TeOF_5^-$, $R^2SO_3^-$ ou $B(R^2)_4^-$, wherein $R^2$ is fluorine or an alkyl or aryl group optionally halogenated; $(R^2SO_2)_2N^-$; $(R^2SO_2)_2C(R^3)^-$, $(R^2SO_2)_3C^-$ wherein $R^3$ is H or $R^2$. The acids can be directly added to the polymer, or be in a latent form. Salts of weak bases such as nitrogenated bases or ethers, are suitable for this use, and the acid form is freed by heat, preferably at temperatures between 40 and 180° C. It is also possible to free the acid thermally from a diazonium salt $RN{=}N^+X^-$ decomposing to lead to the acid HX and nitrogen by extraction of protons from the solvent or the monomer.

Acid esters corresponding to non nucleophilic anions are efficient cationic initiators. They include methyl, ethyl or benzyl derivatives of toluene-, fluoro-, methane- and trifluoromethanesulfonates, and tetramethylene —$(CH_2)_4$— diesters.

In a preferred embodiment, the acids can be freed by the action of actinic radiations on leaving compounds. Actinic radiation includes visible or UV photons, ionizing radiations, like γ rays and β electron beams. Cationic photoinitiators, in other words acid photogenerators, comprise ionic compounds $J^+X^-$, wherein $X^-$ is an anion as defined above and $J^+$ is a cation of the diaryl-iodionium, diarylbromonium, triarylsulfonium, phenacyl-dialkylsulfonium, arene-metallocenium, aryldiazonium type, the organic group being optionally substituted. Two or more $J^+$ cations can be linked together or $J^+$ can be part of a recurring unit of a polymer chain. Another family of photoinitiators or thermal initiators comprise advantageously sulphonic esters of 2-nitro, 2,4-dinitro or 2,6-dinitrobenzyl, in particular 2,4-dinitro or 2,6-dinitrobenzyl toluenesulfonates. These initiators are not ionic, thus easily miscible with the monomers and polymers slightly or non polar.

Other cationic initiators exist, in particular derivatives of allyloxypyridinium salts, which, in the presence of free radical generators, activated thermally or with an actinic radiation, release alkyl or pyridyl cations. There may be mentioned N-[2-ethoxycabonylallyloxy]-α-picolinium hexafluoroantimonate.

The technique of the invention is particularly advantageous for the preparation of polymers in the form of films because of the absence of sensitivity of the cationic polymerization process to oxygen, in particular when compared to other techniques involving radicalar processes. The process is however not limited to such type of moulding. The polymers, before cross-linking, can be molded in various forms, following the addition of a latent cationic polymerization catalyst, which can be activated either by heat or by a penetrating actinic radiation.

It can be interesting to minimize the volume contractions inherent to most polymerization processes, including the cross-linking. The cationic processes involving oxygenated derivatives of dioxolanes of the type spiro-orthoformates or spiro-orthocarbonates are characterized by an increase of volume. Monomers and polymers of the invention bearing such functions that can be used to control the variation of volumes, are exemplified by the following formulas:

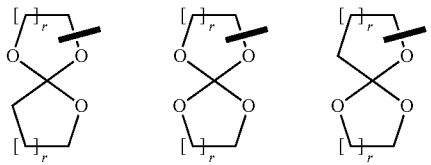

Another advantage brought by the cationic cross-linking groups of the invention, in addition to the complete and controlled cross-linking, is the flexibility of the sub-network obtained. The functions resulting from the cationic cross-linking bearing groups of the type:

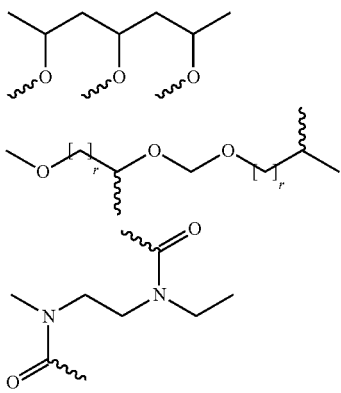

are intrinsically flexible, and the corresponding homopolymers have low glassy transition temperatures ($T_g$). For example, $T_g=-31°$ C. for polyvinylmethyl ether, while que $T_g=+114°$ C. for methyl polymethacrylate. These characteristics can be maintained at the cationic sub-network level of the polymer depending on the choice of the flexible bonds linking the anionic groups to the cationic groups. Simple alkylene $—(CH_2)_n—$ wherein $2 \leq n \leq 12$ and oxyalkylene $—[CH_2OCH(R)]_n—$ wherein $1 \leq n \leq 6$, are particularly preferred to form divalent organic bonds insuring the link between the anionic groups and the cationic groups in the monomer and/or the resulting polymer.

The polymers of the present invention can be homo- or statistic copolymers incorporating monomers with double functionality and one or more other monomers. For example, a terpolymer containing monomers A, B and C in molar ratios a, b, and c, is denoted $A_a$-stat-$B_b$-stat-$C_c$. They can be bloc polymers of the type A-bloc-B or A-bloc-B-bloc-A, A-bloc-B-bloc-C, each segment A, B or C incorporating at various rates the double functionality monomers. In a variation, only A, B or C includes, in the form of a homopolymer or copolymer, at least one double functionality monomer. It is understood that the polymers of the invention are not limited to three monomers, and that any person skilled in the art will appreciate the possible variations offered by the living character of anionic polymerization. Another possibility is to form star polymers or dendrimers from polyfunctional anionic initiators of the type $T(A_a$-stat-$B_b$-stat-$C_c)_t$, $T(A$-bloc-$B)_t$, or $T(A$-bloc-B-bloc-$A)_t$, or even $T(A$-bloc-B-bloc-$C)_t$, T being a polyfunctional radical of valence t, $2 \leq t \leq 10^4$, preferably, $2 \leq t \leq 10$ for star structures, and up to $10^4$ for dendrimers. Branched polymers can be obtained by using low rates of a monomer having more than one reactive functionality in anionic polymerization.

The molding and cross-linking step can precede or be simultaneous with the addition of various additives, for example, a dispersion of solids, in the form of powders, flakes of fibers, for changing the rheological properties during the moulding and/or confer improved mechanical characteristics to the finished product as well as fire retardant properties. To that end, it can be mentioned silica dispersions in the form of nanoparticles, carbon black, simple oxides like magnesia, or complexes like $LiAlO_2$, metallic nitrides and carbides, flaked silicates, in particular micas, hectorite, montmorillonite, vermiculite, graphite, including in expanded form; fluoroaluminates complexes of the type $KAlF_4$, fibers of the polyolefine or polyimide type, including those aromatics, carbon fibers in particular those obtained from pyrolysis of organic materials or ceramic fibers comprising oxides, nitrides or carbides or oxynitrides or oxycarbides, optionally in the form of woven or non-woven layer. Additives conferring other properties specific to the polymer can also be added. For example, additives having an ionic or electronic conductivity, such as alumina β or β", lithium nitride, any form of carbon, conjugated polymers, in particular derivatives of benzene, thiophene, pyrrole and condensed heteroaromatic rings. Perovskite structure additives can contribute to increase the dielectric constant by inducing piezoelectric properties to the resulting composite material.

The molar proportion of double functionality monomer can be chosen between 0.1 and 100% molar depending on the cross-linking density desired. Preferred compositions according to the invention comprise between 1 and 35% molar of double functionality monomer.

Liquids or plasticizers increasing the flexibility of the polymer in a finished state or during moulding can also be added. Such liquids or plasticizers are numerous and well-known to anyone skilled in the art. In general, materials are selected for their compatibility with the polymer chain and their low volatility. There can be mentioned organic polyacid esters such as phtalates, citrates, α,ω-diacids of alkyls of 3 to 12 carbon atoms or alkylene glycols of 2 to 18 carbon atoms, and esters of phosphoric or phosphonic acids, which confer fire retardant properties.

The addition of plasticizers further allows the increase, if necessary, of the conductivity of polymer electrolytes at low temperatures. The plasticizer is then chosen with respect to its dielectric constant as well as for its electrochemical stability in the conditions in which the polymer electrolyte will be used. Most useful plasticizers for that purpose comprise cyclic and acyclic carbonates, in particular ethylene and propylene carbonates, dimethyl, diethyl, ethyl-methyl and methyl-propyl carbonates; γ-butyrolactone; carboxylic acid esters such as formiates, acetates, alkyl propionates of from 1 to 6 carbon atoms; tetraalkylsulfamides; dialkylated ethers of mono, di, tri and tetraethylene glycols comprising alkyl groups of from 1 to 8 carbon atoms; dialkylated ethers of oligooxyethylene of weights inferior to 2000 g/mol, these alkyl groups having between 1 and 18 carbon atoms. Such plasticizers can be used alone or in combinations thereof.

The concentration of plasticizer can vary, generally between 0.5 and 90% by weight, and preferably between 3 and 70% by weight. High concentrations of plasticizer give materials with a high conductivity. The mobility of the chain becoming important, this translates by a noticeable loss of mechanical properties. The strong cross-linking density obtained with the polymers according to the invention is an advantage to maintain good mechanical properties.

The plasticizers added can also react during the cationic cross-linking reaction. The plasticizer or plasticizers added to the polymer must then contain at least one cationic polymerization reactive function. Various plasticizers of that type are known and/or commercially available, in particular those bearing vinyl ether functions. There may be mentioned vinyl ether of glycols, in particular those of butanediol, di-, tri-, and tetraethylene glycol and their monoalkyl-ethers, and trimethylolpropane. A particularly interesting additive, because of its high dielectric constant and its facility to dissolve in polar compounds, metallic or onium salts, including cationic photoinitiators, is propenyl-propylene carbonate ether

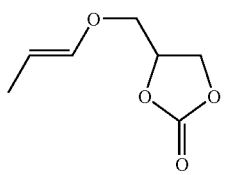

Any other coloring agent, anti-oxidant or anti-UV additive known to those skilled in the art and compatible with the monomer structures and polymers obtained therefrom can be used for the polymers of the invention.

The cross-linking can also be performed in the presence of cationic polymerization reactive cycles, such as epoxides, 1,3-dioxolane, 1,3-dioxane, 1,3-dioxepane and their derivatives, spiranes of the orthoformate or orthocarbonate type as defined above, for example derivatives of mono- and di-formal pentaerytritol. When Y is a vinyl ether, it is further possible to incorporate monomers with electron-poor double bonds. Examples include fumarates, maleates, maleic anhydride, maleimide, and as well as acrylates and methacrylates. These compounds form, with vinyl ethers, charge transfer complexes, and their polymerization leads to the formation of an alternate polymer forming the cross-linking sub-network. Such type of polymerization is spontaneously activated by heat or free radical sources, either thermally generated or generated through actinic radiations, even in the presence of a photoinitiator. The maleimide derivatives in particular provide complexes spontaneously polymerizable in the presence of UV and barely sensitive to oxygen. The compounds can be monofunctional, or bifunctional such as

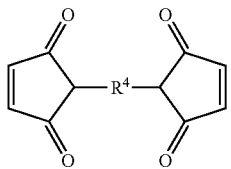

wherein $R^4$ is an alkylene radical comprising from 2 to 18 carbon atoms or oxyalkylene —$CH_2CH_2(OCH_2CH_2)_nOCH_2CH_2$— wherein n varies between 0 and 60.

The use of the compounds of the invention for the preparation of polymer electrolytes represents a particularly preferred embodiment. Such polymer electrolytes have various applications in the field of electrochemistry. They also have anti-static properties that do not require the addition of absorbing conductive powders. As stated above, polyethers are preferred materials because of their dissociating and solubilizing power towards metallic salts or nitrogenated protonated bases (ammonium, imidazolium, guanidinium, etc.). The polymer may be linear, star shaped, or comb-like with lateral chains. Linear polymers are easier to obtain by co-polymerization of one or more solvating epoxides with a monomer of the invention having an epoxide as group A. Solvating epoxides preferably comprise ethylene oxide, propylene oxide and butylene oxide. Ethylene oxide is particularly preferred because of its high complexing power and its strong anionic polymerization reactivity, thus allowing control of the molecular weight.

Depending on the conditions of use of the polymer electrolyte, it may be preferable to minimize the degree of crystallinity resulting from the inclination of the ethylene polyoxide segments to form organized domains, the existence of which being prejudicial to the conductivity. For this reason, the preparation of terpolymers between ethylene oxide, the starting monomer and a terpolymer is chosen. The terpolymer preferably comprises propylene oxide, butylene oxide, methylglycidylether, allylglycidylether, or a monomer bearing an ionic function such as

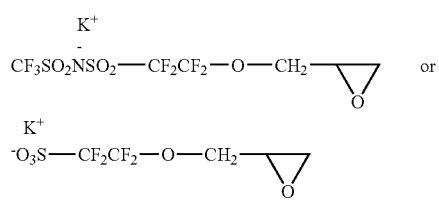

preferably in a proportion of from 0.5 to 25% molar. Potassium is advantageous because it does not interfere with the cationic polymerization and can be exchanged later for other ions, such as lithium cation.

The monomer of the polymer electrolytes according to the invention preferably comprise the compounds

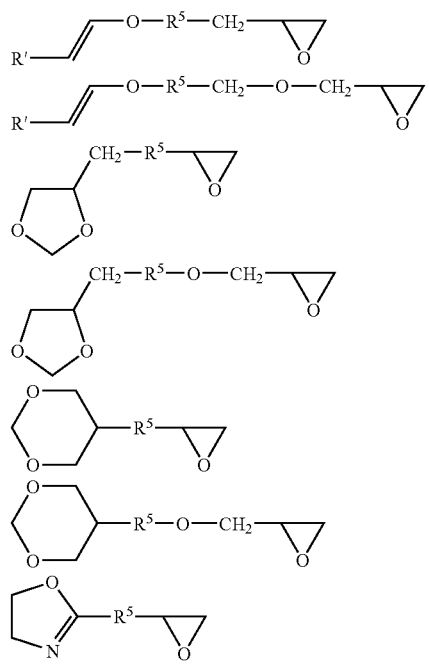

-continued

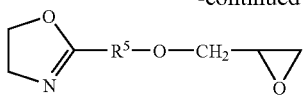

wherein $R^5$ represents a divalent alkyl or oxa-alkyl of from 0 to 12 carbon atoms; and R' is as defined above.

$R^5$ is preferably —$CH_2$—, —$C_2H_4$—, —$C_4H_8$—, —$C_6H_{12}$—, —$C_2H_4OC_2H_4$— or —$C_2H_4OC_2H_4OC_2H_4O$—, and R' preferably comprises hydrogen, methyl or ethyl. When $R^5$ is —$CH_2$—, R' is preferably methyl or ethyl. The corresponding monomers are easily accessible from commercial allyl glycidyl ether by isomerization of the double bond in the presence of $RuCl_2$ with phosphines or iron pentacarbonyl derivatives.

In another embodiment of the polymer electrolytes, anionic polymerization of styrene is used to form a polymer chain with lateral ethylene oxide chain. The general formula of such compounds is:

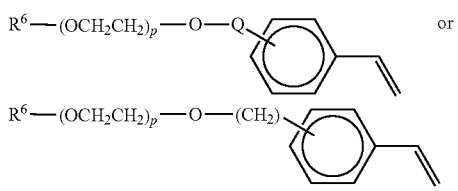

wherein p varies between 2 and 60;

$R^6$ is a monovalent alkyl of from 1 to 18 carbon atoms or a monovalent aryl of from 5 to 18 carbon atoms;

Q is $(CH_2)_q$, —CO— ou —$SO_2$—; and q varies between 0 and 4.

A preferred example of such compound is when Q is $(CH_2)_q$ and q is 1, which can be easily prepared by reacting an alkoxy oligooxyethylene alkaline metal derivative $R^6(OCH_2CH_2)_pOM$ wherein M is Li, Na, K on ortho- or para-chloromethylstyrene.

The monomers allowing the preparation of the preferred polymers of the invention comprise:

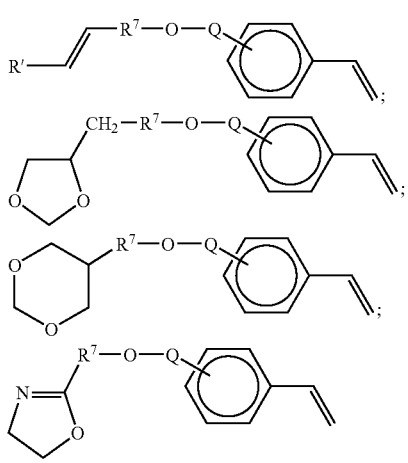

wherein R' and Q are as defined above, and $R^7$ is $R^5$.

Particularly preferred compound are those wherein (—$CH_2$—)$_q$, and q is 1.

It could be advantageous to incorporate a styrene type terpolymer to introduce variations in the $T_g$, the adhesion, the polarity, etc. Vinylbenzene derivatives having various functionalities are preferred, and these derivatives are numerous and well-known to those skilled in the art. Functionalities of interest comprise those with polar groups for changing the local dielectric constant, for example $NO_2$, RCO and RCOO, or changing the surface tensions, for example alkyl chains of more than 8 carbon atoms. Halogens act on the inflammability. It is of interest to incorporate monomers with ionic functions to induce ionic conductivity, mainly because of the cations, which are the most interesting for electrochemical applications. There may be mentioned the monomer salts:

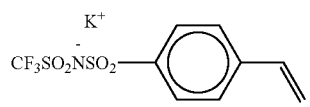

In a further preferred embodiment of the polymer electrolytes, the anionic polymerization of a double bond activated by a carbonyl group is used to form a polymer chain with a lateral ethylene oxide chain. The general formula of the main monomer allowing the synthesis of such polymers is:

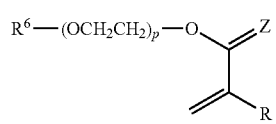

wherein Z, R, $R^6$ and p are as defined above.

In a particularly preferred embodiment, Z is O and R is methyl.

Other preferred monomers for the preparation of the polymers according to the invention comprise:

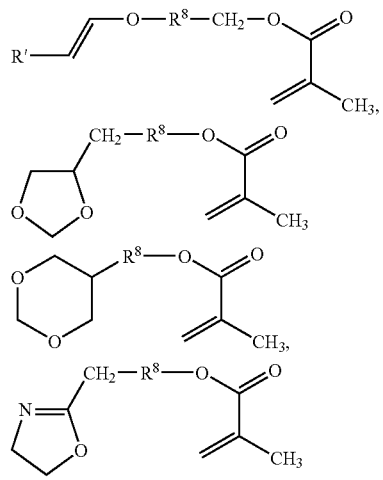

wherein

R' is as defined above and $R^8$ is $R^5$.

As mentioned above, it is of interest to incorporate monomers comprising ionic functions. In such a case, there can be mentioned monomer salts:

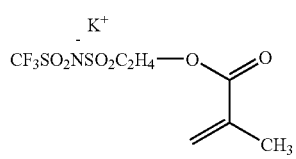

In the preparation of the above polymer electrolytes, conductivity is insured by a salt dissolved in the chain solvating the polyether segments. Generally, the salts are chosen from metallic salts or salts of a nitrogenated protonated base, for example ammonium, imidazolium, guanidinium, that are susceptible of freeing $M^{z+}$ cations and an anion selected preferably from weakly basic and non nucleophilic anions such as $ClO_4^-$, $BF_4^-$, $PF_6^-$, $AsF_6^-$, $SbF_4^-$, $R_fSO_3^-$, $C_nF_{2n+1}SO_3^-$ wherein n varies between 0 and 8, $(R_xSO_2NSO_2R'_x)^-$, $(R_xSO_2C(SO_2R'_x)R_x")^-$, anions derived from cyclopentadiene and its aza analogs bearing electro-attracting groups, anions derived from pyrimidine-trione or 1,3-dioxane-4,5-dione bearing electro-attracting groups, in particular of the type CN or $CF_3SO_2$, and malonitrile derivatives, wherein $R_x$ and $R_x'$ are the same or different and at least one has electronegative atoms such as halogen, and in particular such as that at least one $R_x$ and $R_x'$ is equal to $C_nF_{2n+1}$ wherein n varies between 0 and 8, $R_x"$ being either $R_x$, $R_xSO_2-$ or $R_x'SO_2^-$. Most preferred anions comprise $ClO_4^-$, $BF_4^-$, $PF_6^-$, $CF_3SO_3^-$, $(FSO_2)_2N^-$, $(CF_3SO_2)_2N^-$, $(C_2F_5SO_2)_2N^-$, $[(CF_3SO_2)_2CH]^-$, $[CF_3SO_2)C(CN)_2]^-$, $[(CF_3SO_2)_3C]^-$, $(CF_3SO_2)NSO_2N(R^9)_2)^-$ wherein $R^9$ is an alkyl of from 1 to 30 carbon atoms, anions derived from 4,5-dicyano-1,2,3-triazole, 3-5-bistri-fluorométhyl-1,2,4-triazole, or tricyanomethane. The concentration of salt is preferably expressed in terms of the ratio of the number of oxygens of the oxyethylene segments per cation (O/M). Generally, this number is comprised between 0.5 and 1000.

A great number of cations or mixtures thereof gives solutions in the polymers of the invention. Cations of lithium, sodium, potassium, calcium, tin, ammonium and imidazolium, are preferred. Lithium ion and mixtures of lithium and potassium ions are particularly preferred for electrochemical applications.

The anionic portion or the cationic portion of the salt can be part of a macromolecular chain, including that of the polymer of the invention, through incorporation of termonomers described above or others, of the ionic type. Polymers wherein at least a portion of the negative charges are fixed on the polymer are particularly useful as solid electrolytes for applications in batteries and accumulators, supercapacity or electrochromic systems.

As stated above, the polymers of the invention can be cross-linked until high cross-linking rates are achieved because of the reactivity of the cationic functions of the monomers used. For polymer electrolytes, high cross-linking rates for the purpose of inducing good mechanical properties are useful if the glassy transition temperatures are not raised notably. The flexibility of the bonds linking the anionic chain to the cationic sub-network, as well as the intrinsic flexibility of this sub-network, are significant advantages for polymer electrolytes, as mentioned previously.

Moulding of the polymer electrolytes in thin films is performed conventionally by spreading from a solution, or extrusion. For economical reasons, as well as lower impact on the environment, it is preferred to use quantities of solvents as small as possible. In that respect, polymers with low weight are interesting because their moulding can be carried out from concentrated solutions, or from the pure state. For epoxides, the end of the chains are generally hydroxyls functions. Their higher concentration, in the case of low weight polymers, is prejudicial because these functions are reactive, particularly towards lithium. An advantage of the cationic cross-linking is the possibility of neutralizing the hydroxyl functions to form acetal bonds stable to potentials close to those of lithium participating to the cross-linking. Such possibility is exemplified below in the case where the cationic functions are vinyl ethers:

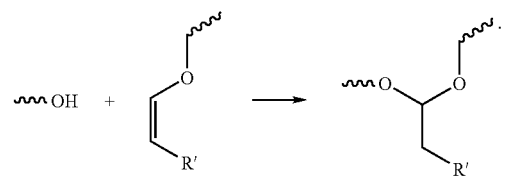

The polymers of the present invention can be used in combination with at least one salt $M^{n+}X_n^-$, wherein $M^{n+}$ is an inorganic, organic or organometallic cation of charge n, and $X^-$ is a monovalent anion, and wherein 2 or more $X^-$ can be linked together with covalent chains or chains belonging to a polymer. Such a combination is useful in a system for storing electric energy such as a primary or secondary generator, or a super-capacity comprising at least one negative electrode and at least one positive electrode, the latter comprising at least in part the ionic compound. The positive electrode may further comprise another electrode material such as vanadium oxides $Li_yVO_x$ wherein ($2x-5 \leq y \leq 2x-3$; $2.15 \leq x \leq 2.5$), $Li_yN_{1-x-z}Co_xAl_zO_2$ wherein $0 \leq x+z \leq 1$ and $0 \leq z \leq 1$, manganese spinels $Li_yMn_{2-x}M_xO_4$ wherein M is Li, Cr, Al, V, Ni, $0 \leq x \leq 0.5$ and $0 \leq y \leq$, organic polydisulfides, polyquinones such as rhodizonates, FeS, $FeS_2$, iron sulfate, iron and lithium phosphates and phosphosilicates of the olivine or Nasicon structure, or products of substitution of iron with manganese, used alone or in mixtures.

The following examples are provided to illustrate preferred embodiments of the invention, and should not be construed as limiting the scope thereof.

Example 1

In a 500 ml reactor, 110 g of a commercial trifunctional polymer prepared by anionic polymerization of ethylene oxide from 1,1,1-tris(hydroxymethyl)propane are dissolved in 250 mL of THF. 33.6 g of potassium tertiobutoxide are added, followed by 86 g of 4-vinyloxy-glycidoxy-butane:

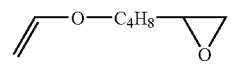

The mixture is heated 3 hours at 50° C. At the end of the reaction, termination of the chain is obtained from methyl groups from the addition of 37 g of methyl sulfate. The block polymer is of formula:

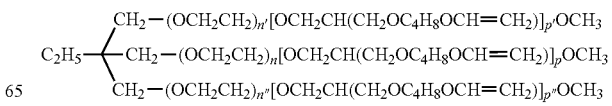

wherein n+n'+n" is of the order of 20; and p+p'+p" is of the order of 5.

The polymer solution is centrifuged and the THF is removed. Purification is carried out by solubilization in 200 mL of dichloromethane and extraction in water (400 mL). The polymer is then precipitated in 2 L of ethyl ether maintained à −20° C.

A polymer electrolyte is obtained by dissolving the polymer thus obtained in a mixture of acetone (55% by weight) in the presence of lithium perchlorate to obtain a ratio of oxygen of the oxyethylene groups per lithium ion of 16:1. To this solution, are added 1% by weight with respect to the polymer in the solution, of $(C_4H_9OC_6H_4IC_6H_5)^+[FSO_2)_2N]^-$. The polymer is spread from the solution in the form of a film of a thickness of 35 μm on a high density polyethylene substrate, and cross-linked by UV irradiation at 365 nm for 20 seconds, corresponding to an energy of 35 mJoules/cm². The polymer obtained is a resilient elastomer with a conductivity of $10^{-5}$ Scm$^{-1}$ à 25° C.

Example 2

Commercial glycerol formal is separated in its two isomers (4-hydroxymethyl-1,3-dioxolane and 5-hydroxy-1,3-dioxane) according to the method of Hibbert et al. [*J. Am. Chem. Soc.* 50, 3120 (1928)]. To 10.4 g of 4-hydroxymethyl-1,3-dioxolane (isomer 1) are added under vigorous agitation 5.8 g of KOH grounded in a mixer, 200 mg of tetrabutylammonium chloride acting as a phase transfer catalyst. 9.2 g of epichlorhydrine are then added progressively to allow the temperature to remain below 30° C. by external cooling. KCl formed is separated by filtration and the (4-glycidoxymethyl)-1,3-dioxolane obtained is purified through two distillations.

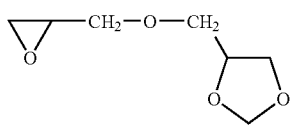

This monomer is copolymerized with ethylene oxide in the conditions of example 12 by using potassium tert-butoxide as the anionic initiator. The molar ratio of the monomers is selected from 95 (EO) to 5 (bifunctional monomer). The polymer is precipitated in hexane. The molecular weight measured by steric exclusion chromatography is 45×10³ g. A polymer electrolyte is prepared by dissolving the salt Li(CF₃SO₂)₂N in a concentration such that O/Li=24:1 in a common solvent, acetonitrile, to which is added 1% of the salt of dimethyl-phenacyl-sulfonium $[C_6H_5(=O)CH_2S(CH_3)_2]^+$ $(CF_3SO_2)_2N^-$. The solution is spread to form after evaporation of the solvent, a film of a thickness of 24 μm. Cross-linking is performed by irradiation with a UV lamp of the Hanovia type for a dosage of 40 mJ/cm². The polymer obtained is also a conductive elastomer ($10^{-5}$ Scm$^{-1}$ at 25° C. and 1.3×10$^{-3}$ Scm$^{-1}$ at 80° C.).

Example 3

Monovinyl Ether Diethyleneglycol (BASF) is Esterified by the Methacryloyle Chloride to Form

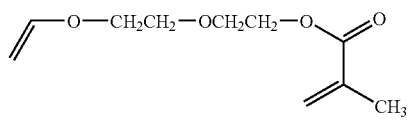

A statistic polymer is obtained by anionic polymerization of this monomer with co-methoxy(oligooxyethylene) methacrylate that has an oxyethylene segment weight of 900. The ratio of the two monomers is 85:15 (oligo-EO/dioxolane). The anionic initiator is phosphazene base P4-t-bu in anhydrous THF. Polymerization is performed at 25° C. in 24 hours. The polymer is precipitated with diethyl ether and purified by two dissolution/precipitation in THF/ether. The polymer is molded in a thin film by spreading from an acetonitrile solution containing lithium trifluoromethanesulfonate in a concentration such that the concentration ratio of the ether-type oxygen atoms brought by the lithium salt is of 20:1. 0.8% by weight of a thermal cationic initiator, 2-nitrobenzyle toluenesulfonate, is then added. Colloidal silica is also added in an amount of 12% by weight of polymer. The mixture's viscosity is adjusted to form after evaporation a film of a thickness of 45 μm. The film thus obtained is cross-linked by heating one hour at 80° C. The polymer electrolyte obtained is a resilient elastomer with a conductivity of 2×10$^{-5}$ Scm$^{-1}$ at 25° C.

Example 4

11.6 g of monovinyl ether 1,4-butanediol (BASF) are treated in 100 mL of THF with 2.6 g of sodium hydride. The solution obtained is reacted under reflux and nitrogen atmosphere with 15.2 g of commercial chloromethyl-4-styrene (Aldrich). The 4-vinyloxybutoxymethyl-4-styrene

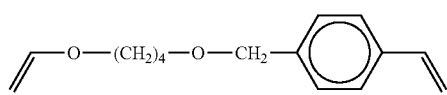

is obtained after filtration and evaporation of THF. The monomer is purified by distillation. A polymer of styrene and 4-vinyloxybutoxymethyl-4-styrene (91:9 molar) is prepared by initiation with sec-butyllithium (5×10$^{-3}$ molar/total of monomers) in toluene at −30° C. After 8 hours the polymer is precipitated in methanol.

The cationic photoinitiator 4-octyloxyoxyphenyl(diphenyl)sulfonium bis(trifluoromethanesulfonyl)imide is prepared by exchange in water between the corresponding sulfonium hexafluorophosphate, and the potassium salt of imide K(CF₃SO₂)₂N. A film is prepared by evaporating a solution of the copolymer of substituted polystyrene and 0.5% by weight of the photoinitiator in toluene to obtain a film of a thickness of 10 mm on an aluminum substrate. The polymer is irradiated with a UV beam at 254 nm at 40 mJ/cm² for 5 seconds. The cross-linked polymer is insoluble in all usual solvents and has an excellent dielectric rigidity.

Example 5

5 g of the styrenic polymer of example 4 and 400 mg of maleic anhydride are solubilized in 15 ml of THF and spread in the form of a film of a thickness of 8 μm on an aluminum substrate. Polymer is submitted to UV beams at 254 nm at a dosage of 60 mJ/cm². The cross-linked film obtained is insoluble in all usual solvents and its adhesion to the aluminum substrate allows its deformation (mandrel test: 4 mm, ASTM standard D 3359 crosshatch adhesion test: 5) without noticeable detachment of the polymer.

Example 6

10.4 g of 5-hydroxy-2,3-dioxane (isomer 2 of Example 2) are reacted with 9.65 ml of methacryoyle chloride in the presence of 8 g of pyridine at 0° C. in 50 ml of THF, to lead to 5-methacryloxy-1,3-dioxane that is purified by distillation.

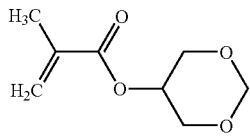

A copolymer of methyl methacrylate, butyl and 5-methacryloxy-2,3-dioxane is prepared by anionic initiation with tetrabutylammonium thiophenoxide (FLUKA) in THF. The molar ratios are 65:25:10. The polymer is precipitated in ethanol and purified by two dissolutions/precipitations in THF:ethanol. A film of this polymer, to which is added 0.8% by weight of 2,4-dinitro-benzyl toluene sulfonate, is obtained by spreading a solution thereof in THF on a polytetrafluoroethylene substrate, and cross-linked by heating 4 minutes at 80° C. This polymer is transparent and insoluble in all usual solvents. At 300° C., the polymer is reconverted to its monomers and can therefore be recycled.

Example 7

2-hydroxyethyloxazoline is prepared by azeotropic dehydration of the salt formed between 3-hydroxypropionic acid and aminoethanol. The 4-(2-methacryloxy-ethyl)-1,3-oxazoline is prepared by reaction of the methacryloyle chloride on the hydroxylated derivative in the presence of triethylamine at 0° C. The monomer is of formula

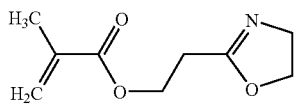

A copolymer of butyl methacrylate and 4-(2-methacryloxy-ethyl)-1,3-oxazoline (90:10 molar) is prepared by anionic polymerization with "phosphazene P4 base" (Fluka) in anhydrous THF for 12 hours. The polymer is precipitated in ethanol. A solution of 10% by weight of this polymer in dichloromethane to which is added 0.5% by weight of Busulfan® (1,4-butanediol dimethanesulfonate) is spread on a polytetrafluoroethylene substrate and the solvent is evaporated. The polymer is heated at 70° C. for 10 minutes under dry air atmosphere. The cross-linking by cationic opening of the oxazoline cycle leads to, after detachment of the substrate, a flexible film transparent and insoluble in usual solvents.

Example 8

13.4 g of commercial 1,2,6-hexanetriol are added to 12.4 ml of diethoxymethane and the mixture is refluxed in the presence of 500 mg of toluenesulfonic acid acting as a transacetalisation catalyst. The ethanol is evaporated at 80° C. and the 4-(4-hydroxybutyl)-1,2-dioxolane obtained is purified by distillation. 7.3 g of this product and 4.6 g of epichlorhydrine are reacted in the presence of 2.8 g of potassium hydroxide (powder) and tetrabutylammonium chloride, to form the monomer 4-[(4-glycidyloxy)-butyl]-1,3-dioxolane

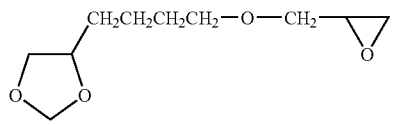

A copolymer of ethylene oxide and this monomer in a molar ratio 93:7 is prepared by anionic initiation with potassium tert-butoxide in THF. The polymer is purified by centrifugation and precipitation in ether. A polymer electrolyte is formed by adding the lithium salt $Li[CF_3SO_2C(CN)_2]$ in a ratio O/Li=18:1. The polymer is cross-linked by adding 0.8% by weight of the initiator $[CH_3CH(CH_3)C_6H_5Fe(C_5H_5)]^+$ $[(FSO_2)_2N]^-$ and subsequent UV irradiation at 40 mJ/cm². The polymer is an elastomer insoluble in all solvents and its conductivity is superior to $10^{-4}$ $Scm^{-1}$ at 55° C.

Example 9

13.2 g of commercial 3-allyloxy-1,2-propanediol, 12 ml of trimethyl-orthoformate and 11.1 ml of γ-caprolactone are heated at 90° C. in the presence of 500 mg of toluenesulfonic acid. The methanol formed and the excess of methyl orthoformate are eliminated by distillation, and the resulting spiroester is purified by distillation. The allyl group is epoxidated by the magnesium salt of monoperoxy-peroxyphtalic acid in acetonitrile. The monomer

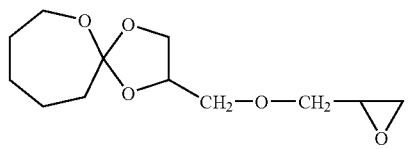 [SMILES: C1CCOC2(CC1)OCC(COCC1CO1)O2]

obtained is purified by distillation and copolymerized with ethylene oxide in the conditions of Example 12 in a molar ratio of 93:7. The polymer obtained is transformed in an ionic conductor by adding the salt $Li[(CH_3)_2NSO_2NSO_2CF_3]$ in a ratio O/Li=14:1. The addition of 4-fluoropyridinium bis-trifluoromethanesulfonate (1% by weight) allows the crosslinking of the polymer at 80° C. with a volume increase.

Example 10

15 g of commercial ω-methoxy(polyethylene glycol) of weight 900 are treated in 100 ml of anhydrous THF with 600 mg of sodium hydride. Following the end of hydrogen evolvement, the excess of sodium hydride is eliminated by centrifugation and 2.5 g of 4-chloromethyl styrene are added to the solution. The sub-product of the reaction (NaCl) is removed by centrifugation and the macromomoner is separated by precipitation in an ether-hexane (50:50) mixture maintained à −20° C. A copolymer of this monomer and of the styrenic vinyl-ether of Example 4 is prepared by anionic polymerization in a molar ratio 85:15 by initiation with sec-butyllithium and tetramethyldiamine to obtain a polymer of a weight of $2.5 \times 10^3$. This polymer is converted to a polymer electrolyte by dissolving $Li(CF_3SO_2)_2N$ in a ratio $O_{ether}/Li$ of 25:1. The polymer is cross-linked by adding $[C_6H_5C(=O(O)CH_2S(CH_3)_2]^+(CF_3SO_2)_2N^-$ (1% by weight) and irradiation at 265 nm at a dosage of 40 mJ/cm².

Example 11

An electrochromic system on a soft substrate is obtained by cathodic spraying of a layer of 700 nm of tungsten oxide on a polyethylene terephtalate (PET) of a thickness of 60 μm, already covered with doped tin oxide ($SnO_2$:F) (100 nm). The counter-electrode is a film of a mixture of oxides $Li_{0.5}TiO_2CeO_2$ (800 nm) on the same substrate. Both electrodes are laminated on each side of a film of a polymer electrolyte according to Example 1 (30 μm). The system thus assembled, which has sealed sides after the addition of current connections, (copper strips of 0.5 cm and 20 μm of thickness) allows a variation of light transmission of the solar spectrum from 85 to 8% by applying a potential of 2V for 300 seconds at 25° C. Polarity inversion brings the transmission back to its original value. The system can be cycled $10^4$ cycles without loss of optical properties.

Example 12

This example illustrates the preparation of a cross-linkable polyepoxide according to the invention. The anionic polymerization is performed in a commercial stainless steel Parr® of a capacity of 2 litres and equipped with an agitator and a hatch for emptying the reactor from the bottom. All the transfer operations are performed under inert atmosphere by using extra dry argon or nitrogen and without oxygen. Reactors with other capacities can be used, as well as those with the interior covered with glass.

The reactor is dried in the following manner. 250 ml of dry toluene are introduced under vacuum and the reactor is subsequently heated at 150° C. for 15 minutes. The hot toluene is then removed by opening the hatch. The reactor is then placed under vacuum for about 10 minutes.

The double functionality monomer

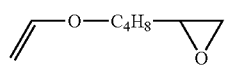

is prepared by reacting monovinylether butanediol (BASF) with epichlorhydrine in the presence of KOH (powder) and a phase transfer agent, i.e., tetrabutyl ammonium hydrogenosulfate. The ethylene oxide is distilled, and the solvents and other monomers are dried on molecular sieve before introduction in the reactor, to reduce their water content to less than 100 ppm, which value is verified by the Karl-Fisher method.

At 20° C., a mixture of 30.03 g of (4-vinyloxybutyl)-glycidylether, 50.05 g of butylene oxide and 120.2 g of ethylene oxide are introduced in the empty reactor cleaned as above. $20 \times 10^{-3}$ mole of potassium tert-butoxide are then added in 20 ml of THF. The temperature is maintained at 25° C. for 23 hours to give 190 g of a liquid mixture at room temperature to which is added 0.2 g of Santonox R® as an antioxidant and stabilizer. According to the proportion initiator:monomer, the molecular weight is lower than 10,000.

Example 13

For this example, the polymerization was performed in a reactor according to the procedure of example 12, and the monomers were dried in the same manner.

In a reactor containing 151 g of toluene, a mixture of 11.39 g of (4-vinyloxybutyl)-glycidylether and 88.6 g of ethylene oxide are added. The reactor temperature is raised to 100° C. and $2 \times 10^{-3}$ moles of potassium tert-butoxide in 2 ml of THF are introduced. The reactor temperature is maintained à 100° C. for 4.5 hours. The pressure lowers from $6.8 \times 10^5$ Pa to $1.2 \times 10^5$ Pa. The temperature is then lowered to 50° C. and 0.1 g of Santonox R® dissolved in 8 ml of toluene are added. The solution is recovered from the reactor through the hatch. After evaporation of the solvent, 89 g of the copolymer are obtained with an average of molecular weight $M_v$ of 39,000. The average molecular weight has been estimated by comparing the viscosity of a solution of the polymer with the viscosity of solutions of polyethylene oxide of known weights.

Example 14

For this example, the polymerization was performed in a reactor according to the procedure of example 12, and the monomers were dried in the same manner.

In a reactor containing 151 g of toluene, a mixture of 11.42 g of (4-vinyloxybutyl)-glycidylether, 3.2 g of butylene oxide and 79.8 g of ethylene oxide are added. The temperature of the reactor is raised to 100° C. and 112 mg of potassium tert-butoxide in 1 ml of THF are added. After 1.5 hours, $5 \times 10^{-4}$ mol of potassium tert-butoxide in 0.5 ml of THF are added. The temperature is maintained at 100° C. for 17 additional hours. The pressure lowers from $5.9 \times 10^5$ Pa to $1.5 \times 10^5$ Pa. The temperature is lowered to 70° C. and 0.1 g of Santonox R® dissolved in 8 ml of toluene are added. The reactor solution is recovered through the hatch. After evaporation of the solvent, 70 g of the copolymer with an average molecular weight of 46,000 are obtained, as measured by the comparative method of example 13.

Example 15

For this example, all the manipulations were performed in a glove box under inert and anhydrous atmosphere (≦1 vpm $H_2O, O_2$). A solution A is obtained by dissolving the polymer of example 13 in 100 ml of a mixture of acetonitrile:toluene (4:1) at a concentration of 0.5 g/cc. After complete dissolution of the polymer, a solution B is obtained by dissolving $LiN(SO_2CF_3)_2$ in solution A to obtain a ratio oxygen of the polymer on lithium, O/Li, of 30:1. A solution C is obtained by dissolving in solution B 1% by weight with respect to the polymer of $[N(SO_2C_2F_5)_2]^-[C_6H_5)_2I]^+$, which is cationic polymerization initiator activated under exposure to UV rays. The polymer matrix is molded in the form of a thin film of about 30 μm on a peelable substrate of polypropylene of 28 μm, by a conventional solvent coating method of solution C, followed by drying. The polymer matrix obtained is subsequently cross-linked under UV irradiation centered on wavelength 365 nm for 10 seconds at a power of 3300 μW/cm². The polymer electrolyte obtained possesses good mechanical properties and is insoluble in a mixture of acetonitrile:toluene (4:1). The polymer matrix is subsequently dried under vacuum at 85° C. for two hours. Measurement by DSC performed on the molten matrix provides a glassy transition temperature at half-height of −65° C. This measurement, as well as that performed for the examples below, indicates that the glassy transition temperature is not affected by the cross-linking. For comparison, PEO homopolymer has a glassy transition temperature of −66° C.

Example 16

In the conditions of manipulation of example 15, a solution A is obtained by dissolving the polymer of example 13 in 100 ml of a mixture of acetonitrile:toluene (4:1) at a concentration of 0.5 g/cc. After complete dissolution of the polymer, a solution B is obtained by the dissolution in solution A of 1% by weight with respect to the polymer of $[N(SO_2C_2F_5)_2]^-$ $[C_6H_5)_2I]^+$. The polymer matrix is molded in the form of a thin film of about 30 µm on a peelable support of polypropylene of 28 µm, by a well-known solvent coating method of solution B. The polymer matrix obtained is cross-linked by UV radiation at 365 nm for 10 seconds at a power of 3300 µW/cm². The matrix obtained possesses good mechanical properties and is insoluble in the solvents of the initial polymer. The polymer matrix is subsequently dried under vacuum at 85° C. for two hours. A measurement by DSC of the melted matrix provides a glassy transition temperature at half-height of −68° C.

Example 17

In the conditions of manipulation of example 15, a solution A is obtained by dissolving the polymer of example 14 in 100 ml of a mixture of acetonitrile:toluene (4:1) at a concentration of 0.5 g/cc. After complete dissolution of the polymer, a solution B is obtained by the dissolution in solution A of 1% by weight with respect to the polymer of $LiN(SO_2CF_3)_2$ to obtain a ratio O/Li of 30:1. A solution C is obtained by dissolving in solution B 1% by weight with respect to the polymer of $[N(SO_2C_2F_5)_2I]^-[C_6H_5)_2I]^+$. The polymer matrix is spread in the form of a thin film of about 30 µm on a support of polypropylene, and cross-linked in the same manner as described above. The matrix obtained possesses good mechanical properties and is insoluble in a mixture of acetonitrile:toluene (4:1). The polymer matrix is subsequently dried under vacuum at 85° C. for two hours. A measurement by DSC of the melted matrix provides a glassy transition temperature at half-height of −64° C.

Example 18

In the conditions of manipulation of example 15, a solution A is obtained by dissolving the polymer of example 14 in 100 ml of a mixture of acetonitrile:toluene (4:1) at a concentration of 0.5 g/cc. After complete dissolution of the polymer, a solution B is obtained by the dissolution in solution A of 1% by weight with respect to the polymer of $[N(SO_2C_2F_5)_2]^-$ $[C_6H_5)_2I]^+$. The polymer matrix is spread in the form of a thin film of about 30 µm on a support of polypropylene. After cross-linking and drying in the conditions of Example 14, the polymer matrix obtained has a glassy transition temperature measured by DSC of −66° C.

Example 19

In the conditions of manipulation of example 15, a solution is obtained by the dissolution in the polymer of example 12 of $LiN(SO_2CF_3)_2$ to obtain a ratio O/Li of 30:1. To this solution is added 1% by weight with respect to the polymer of $[N(SO_2C_2F_5)_2]^-[C_6H_5)_2I]^+$. The polymer matrix is spread in the form of a thin film in accordance with the procedure of Example 15. The polymer matrix is cross-linked for 10 seconds under UV radiations at 365 nm at a power of 3300 µW/cm². The matrix obtained possesses good mechanical properties and is insoluble in the solvents of the polymer prior to the cross-linking. A measurement by DSC of the melted matrix provides a glassy transition temperature of −65° C.

Example 20

This example is provided to illustrate the use of the polymer of the invention to prepare plasticized electrolytes. All the manipulations are performed in a glove box under inert and anhydrous atmosphere ($\leq$1 vpm $H_2O$, $O_2$). The polymer of example 1 is dissolved in a mixture of γ-butyrolactone and ethylene carbonate (50:50 v:v) containing 1 mole per liter of lithium hexafluorophosphate. To this mixture is then added 1% by weight with respect to the polymer of $[N(SO_2C_2F_5)_2]^-[C_6H_5)_2I]^+$. The mixture is spread in the form a of thin film of about 30 µm on a peelable support of polypropylene of 28 µm and is not dried. The plasticized polymer matrix is cross-linked by 10 seconds of irradiation in accordance with the conditions of example 15 to give an elastomer having good mechanical properties even though it contains a high level of liquid plasticizers that are not exuded. the conductivity is greater than $10^{-3}$ Scm$^{-1}$ à 25° C.

Example 21

In the conditions of manipulation of example 15, a solution A is obtained by dissolving the polymer of example 13 in 100 ml of a mixture acetonitrile:toluene (4:1) at a concentration of 0.5 g/cc. After complete dissolution of the polymer, a solution B is obtained by dissolving in solution A the salt $LiN(SO_2CF_3)_2$ to obtain a ratio O/Li of 30:1. A solution C is obtained by dissolving polyoxyethylene of molar weight 200 000 in 100 ml of a mixture of acetonitrile:toluene (4:1) at a concentration of 0.5 g/cc. After complete dissolution of the polyoxyethylene, a solution D is obtained by dissolution in solution C of $LiN(SO_2CF_3)_2$ to obtain a ratio O/Li of 30:1. A solution E is then obtained by mixing a portion of solutions B and D. The proportion of solution B and D is adjusted so that in solution E, the volume proportion of the polymer of solution B is 80%, and the volume proportion of the polymer of solution D is 20%. A solution F is obtained by dissolving in solution E 1% by weight with respect to the polymers of $[N(SO_2C_2F_5)_2]^-[C_6H_5)_2I]^+$. Solution F is spread according to the technique described above. The polymer obtained is cross-linked according to the procedure of Example 15. The resulting matrix possesses good mechanical properties and its glassy transition temperature is −62° C.

Example 22

This example illustrates the addition of a co-polymerizable reactive plasticizer. In the conditions of manipulation of example 15, a solution A is obtained by dissolving the polymer of example 13 in 100 ml of a mixture acetonitrile:toluene (4:1) at a concentration of 0.5 g/cc. After complete dissolution of the polymer, a solution B is obtained by dissolution in solution A of $LiN(SO_2CF_3)_2$ to obtain a ratio O/Li of 30:1. A solution C is obtained by dissolving $LiN(SO_2CF_3)_2$ in triethyleneglycol divinylether (DVE-3), to obtain a ratio O/Li of 30:1. A solution D is obtained by mixing a portion of each of the solutions B and C. The proportion of solution B and C is adjusted so that in solution D, the volume proportion of the polymer of solution B is 80%, and the volume proportion of the polymer of solution C is 20%. A solution E is obtained by the dissolution in solution D of 1.2% by weight with respect to the polymers of $[N(SO_2C_2F_5)_2]^-[C_6H_5)_2I]^+$. Solution E is spread in the form a thin film according to the procedure mentioned previously. The polymer matrix obtained is cross-linked by 10 seconds of UV irradiations at 365 nm at a power of 3300 µW/cm². The film possesses good mechanical properties and is insoluble in the solvents of the polymer. A similar polymer is obtained by replacing the DVE-3 of solution C with trimethylolpropane trivinylether. The mixture of the solutions B and C is made with proportions of 70:30.

Example 23

In the conditions of manipulation of example 15, an electrochemical generator is fabricated by using a 30 μm thick negative electrode of metallic lithium laminated on a current collector of nickel of 8 μm. The separator is made of the polymer matrix of example 19. The positive electrode contains a mixture of vanadium oxide powder, carbon black (Shawinigan Black®) and a polyether-based terpolymer containing $LiN(SO_2CF_3)_2$ in a molar ratio of O/Li of 30:1, the positive electrode having a capacity of 6 coulombs/cm². The composite material is spread from the solution on an 8 μm thick aluminum current collector to give a 45 μm thick film. The electrochemical generator is assembled by heat pressing under vacuum at 80° C. After 12 cycles at 80° C., the generator has a very good cycling behaviour with respect to the coulombic efficiency and a capacity that remains constant.

Example 24

In the conditions of manipulation of example 15, solution A is obtained by dissolving lithium hexafluorophosphate in the polymer of example 1 to obtain a ratio O/Li of 30:1. A solution B is obtained by adding 1% by weight with respect to the polymer of $[N(SO_2C_2F_5)_2]^-[C_6H_5)_2I]^+$ in solution A. The polymer matrix is moulded in the form of a thin film about 30 μm on a peelable polypropylene substrate of 28 μm by coating of solution B. The polymer matrix obtained is subsequently cross-linked under UV irradiation at 365 nm for 10 seconds at a power of 3300 μW/cm².

An electrochemical generator is fabricated by using a negative electrode containing graphite in a weight fraction of 90% and a polymer of vinylidene-co-hexafluoro propene fluoride, in a weight fraction of 10%. The negative electrode possesses a capacity of 3.56 C/cm². The electrode is obtained by coating in solvent phase (acetone) on a 16 μm thick copper current collector to give a film of 56 μm. The separator comprises a polymer membrane as defined in the preceding paragraph (polymer membrane of a thickness of 15 μm containing lithium hexafluorophosphate in a molar ratio of O/Li of 30:1). The positive electrode contains a mixture of lithium cobaltite $LiCoO_2$ in a weight fraction of 91.6%, carbon black in a weight fraction of 2.7% and a polymer of vinylidene-co-hexafluoro propene fluoride in a weight fraction of 5.7%. The positive electrode has a capacity of 4.08 C/cm². The electrode is obtained by coating in solvent phase (acetone) on an 8 μm thick aluminum current collector to provide a film of a thickness of 49 μm. At the time of assembling the electrochemical generator, the separator is immersed 30 minutes in a mixture of solvent ethyl-methyl carbonate/ethylene carbonate (1:1) containing lithium hexafluorophosphate at a concentration of 1 molar, and the cathode and anode are immersed 10 minutes in the same solution. Following the immersion, the solvent occupies 41% of the volume of the separator, 51% of the volume of the cathode and 45% of the volume of the anode. The electrochemical generator is subsequently quickly assembled by light pressing of the negative electrode, the separator and the positive electrode at 25° C., and placed in a sealed bag. After 12 cycles at 25° C., the generator shows excellent cycling behaviour with respect to the coulombic efficiency and a capacity that remains constant.

Example 25

In the conditions of manipulation of example 15, solution A is obtained by dissolution of the polymer of example 12 in a mixture of γ-butyrolactone with ethylene carbonate (50:50 v/v) containing lithium hexafluorophosphate at a concentration of 1 molar, to obtain a volume ratio of 50% of polymer and 50% of the mixture of solvents. A solution B is obtained by adding to solution A 1% by weight with respect to the polymer of $[N(SO_2C_2F_5)_2]^-[C_6H_5)_2I]^+$.

An electrochemical generator is fabricated by using a negative electrode containing graphite in a weight fraction of 58%, a polymer of vinylidene co-hexafluoro propene fluoride in a weight fraction of 5.8%, the polymer of example 12 in a weight fraction of 3.2% and a mixture of γ-butyrolactone, ethylene carbonate (50:50 v/v) containing 1 molar of $LiPF_6$, in weight fraction of 33%. Also added is 1% by weight with respect to the polymer of example 12 of $[N(SO_2F)_2]^-[C_5H_5)NH]^+$, which is a cationic polymerization initiator that can be activated thermally. The electrode is obtained by coating in solvent phase (2-butanone) on a 16 μm thick copper collector, followed by heating for 3 hours at 80° C. to cross-link the polymer of Example 12 in the electrode. The negative electrode possesses a capacity of 3.6 C/cm². The positive electrode contains a mixture of iron and lithium phosphate $(LiFePO_4)$ in a weight fraction of 58%, a polymer of vinylidene fluoride co-hexafluoro propene in a weight fraction of 5.8%, the polymer of example 12 in a weight fraction of 3.2% and a mixture of γ-butyrolactone/ethylene carbonate (50:50) containing one molar of lithium hexafluorophosphate, in a weight fraction of 33%. Also added is 1% by weight with respect to the polymer of example 12 of $[N(SO_2F)_2]^-[C_5H_5)NH]^+$. The electrode is obtained by coating in solvent phase (butanone) on an 8 μm thick aluminum current collector followed by heating for 3 hours at 80° C. to cross-link the polymer of example 12 in the electrode. The positive electrode has a capacity of 3.99 C/cm². Solution B is spread by direct coating on the negative electrode in the form of a thin film of 15 μm and cross-linked under UV irradiation for 10 seconds at 365 nm at a power of 3300 μW/cm². The electrochemical generator is then rapidly assembled by slight pressing at 25° C. of the half-cell constituted by the negative electrode, the separator and the positive electrode, and placed in a sealed bag. After 8 cycles at 25° C., the generator possesses excellent cycling behaviour with respect to the coulombic efficiency and a capacity that remains constant.

Example 26

For this example, the polymerization was performed in a reactor according to the procedure of example 12, and the monomers were dried in the same manner.

1-propenyl glydicyl ether is prepared by isomerization of commercial allyl-glycidyl ether with $RuCl_2[P(C_6H_5)_2]_3$ catalyst at 0.5% molar at 120° C. In the empty reactor deprived of water and impurities and containing 500 g of toluene, 5.67 g of 1-propenyl glycidyl ether, 16.1 g of butylene oxide and 177.6 g of ethylene oxide are introduced at room temperature. The reactor temperature is raised to 99° C., and $2 \times 10^{-3}$ moles of potassium tert-amylate in 2 ml of toluene are added. The temperature is maintained at 99° C. for 24 hours.

The pressure lowers from $12.3 \times 10^5$ Pa to $3.4 \times 10^5$ Pa. Temperature is lowered to 45° C. and 0.2 g of Santonox R® dissolved in 8 ml of toluene are then added. The solution is recovered from the reactor through the hatch. After evaporation of the solvent, 180 g of the copolymer of an average molecular weight of 44 000 is obtained as measured by the comparative method of example 13.

Example 27

For this example, the polymerization was performed in a reactor according to the procedure of Example 12, and the monomers were dried in the same manner.

In the empty reactor deprived of water and impurities, 20.05 g of 1-propenyl glycidyl ether, 60.10 g of butylene oxide and 119.9 g of ethylene oxide are introduced at room temperature. $20 \times 10^{-3}$ moles of potassium tert-butanolate in 20 ml of THF are then added and the reactor temperature is maintained at 25° C. for 26 hours. The pressure lowers from $6.3 \times 10^5$ Pa to $3.6 \times 10^5$ Pa. 0.2 g of Santonox R® dissolved in 8 ml of toluene are then added. 180 g of a viscous liquid mixture is extracted from the hatch of the reactor. Considering the proportion of monomer and potassium tert-butanolate, the molecular weight is estimated to be of the order of 10 000.

Example 28

In the conditions of manipulation of example 15, a solution A is obtained by dissolving the polymer of example 26 in 100 ml of a mixture of acetonitrile:toluene (4:1) at a concentration of 0.5 g/cc. After complete dissolution of the polymer, a solution B is obtained by the dissolution in solution A of $LiN(SO_2CF_3)_2$ to obtain a ratio O/Li of 30:1. A solution C is obtained by dissolving in solution B 1% by weight with respect to the polymer of $[N(SO_2C_2F_5)_2]^-[C_6H_5)_2I]^+$. The polymer matrix is spread in the form of a thin film in accordance with the procedure described above. The polymer matrix obtained is the cross-linked under UV irradiation for 12 seconds at 365 nm at a power of 3200 µW/cm². The matrix obtained has good mechanical properties and is insoluble in the polymer solvents prior to irradiation. The polymer matrix is subsequently dried under vacuum at 85° C. for two hours. A measurement by DSC of the melted matrix provides a glassy transition temperature of −62° C.

Example 29

In the conditions of manipulation of example 15, a solution A is obtained by dissolving $LiN(SO_2CF_3)_2$ in the polymer of example 20 to obtain a ration O/Li of 30:1. A solution B is obtained by the dissolution in solution A of 1% by weight with respect to the polymer of $[N(SO_2C_2F_5)_2]^-[C_6H_5)_2I]^+$. Solution B is spread in the form of a thin film as described above, and cross-linked under Lw irradiation for 12 seconds at 365 nm at a power of 3200 µW/cm². The matrix obtained has good mechanical properties and is insoluble in the polymer solvents prior to irradiation. The DSC glassy transition temperature measured is −64° C.

Example 30

In the conditions of manipulation of Example 15, a solution A is obtained by dissolving the polymer of Example 27 in a mixture of tetraethylsulfamide-ethylene carbonate (60:40) containing lithium hexafluorophosphate in a concentration of 1 molar, to obtain a ratio (volume) of 50% polymer and 50% mixture of solvent. A solution B is obtained by the dissolution of 1% by weight with respect to the polymer of $[N(SO_2C_2F_5)_2]^-[C_6H_5)_2I]^+$. Solution B is spread to form a 30 µm thick film on a polypropylene substrate, without evaporation of the solvents. The polymer matrix obtained is cross-linked under UV irradiation for 12 seconds at 365 nm at a power of 3200 µW/cm². The matrix obtained has good mechanical properties and does not exude any solvent.

While the invention has been described in connection with specific embodiments thereof, it will be understood that it is capable of further modifications and this application is intended to cover any variations, uses or adaptations of the invention following, in general, the principles of the invention and including such departures from the present description as come within known or customary practice within the art to which the invention pertains, and as may be applied to the essential features hereinbefore set forth, and as follows in the scope of the appended claims.

What is claimed is:

1. An electrochemical cell comprising an electrolyte, wherein the electrolyte comprises at least in part an ionic conduction material comprising at least one cross-linked polymer obtained by anionic polymerization initiation followed by cationic cross-linking of a monomer of general formula:

$$(A)_nQ(Y)_p$$

wherein

Q represents a bond, —CO—, —SO$_2$—, or an organic radical of n+p valence which is non reactive towards reagents initiating anionic or cationic polymerization, said organic radical being selected from alkyl, alkylaryl, arylalkyl, optionally comprising oxa or aza substituents, and comprising from 1 to 30 carbon atoms;

A is selected from the group consisting of:

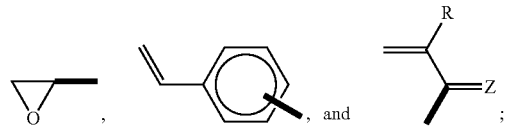

Y is selected from the group consisting of:

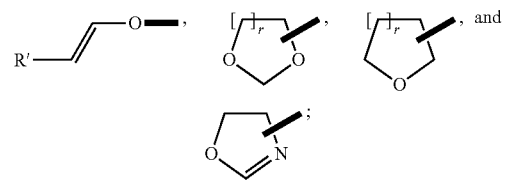

and said Y is non-reactive toward reagents initiating anionic polymerization Z represents O or CH$_2$;

R represents H, an alkyl or oxa-alkyl radical of from 1 to 12 carbon atoms, CN or CH$_2$COOR$^1$ wherein R$^1$ is H or an alkyl or oxa-alkyl radical of 1 to 12 carbon atoms;

R' represents H or an alkyl radical of 1 to 12 carbon atoms;

r varies between 1 and 6;

n varies between 1 and 3; and p varies between 1 and 6; and at least one salt $M^{n+}X^-_n$, wherein $M^{n+}$ is an inorganic, organic, or organometallic cation of charge n, and X$^-$ is a monovalent anion, and wherein two or more anions X$^-$ can be linked together with covalent chains or chains belonging to a polymer chain.

2. An electrical energy storage system of the primary or secondary generator type, or super-capacity, comprising at least one negative electrode and at least one positive electrode comprising at least in part an ionic conduction material comprising:

at least one cross-linked polymer obtained by anionic polymerization initiation followed by cationic cross-linking of a monomer of general formula:

$$(A)_nQ(Y)_p$$

wherein

Q represents a bond, —CO—, —SO$_2$—, or an organic radical of n+p valence which is non reactive towards reagents initiating anionic or cationic polymerization, said organic radical being selected from alkyl, alkylaryl, arylalkyl, optionally comprising oxa or aza substituents, and comprising from 1 to 30 carbon atoms;

A is selected from the group consisting of:

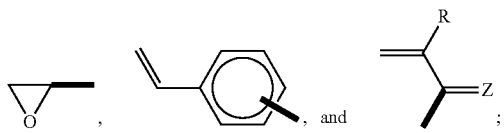

Y is selected from the group consisting of:

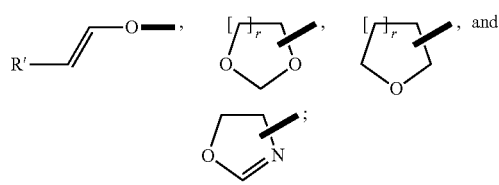

and said Y is non-reactive toward agents initiating anionic polymerization;

Z represents O or CH$_2$;

R represents H, an alkyl or oxa-alkyl radical of from 1 to 12 carbon atoms, CN or CH$_2$COOR$^1$ wherein R$^1$ is H or an alkyl or oxa-alkyl radical of 1 to 12 carbon atoms;

R' represents H or an alkyl radical of 1 to 12 carbon atoms;

r varies between 1 and 6;

n varies between 1 and 3; and p varies between 1 and 6; and at least one salt $M^{n+}X^-_n$;

wherein $M^{n+}$ is an inorganic, organic, or organometallic cation of charge n, and $X^-$ is a monovalent anion, and wherein two or more anions $X^-$ can be linked together with covalent chains or chains belonging to a polymer chain.

3. A system according to claim 2 wherein the cations participating to the electrode reactions are lithium ions.

4. A system according to claim 2 wherein the negative electrode comprises metallic lithium or an alloy thereof, optionally in the form of a nanometric dispersion in lithium oxide, double nitrides of lithium and a transition metal, low potential oxides of general formula $Li_{1+y}Ti_{2-x/4}O_4$, wherein $x \geq 0$ and $y \leq 1$, $MoO_2$, $WO_2$, carbon and carbonated products obtained from organic material pyrolysis, lithium-aluminum or lithium-silicon alloys.

5. A system according to claim 2 wherein the positive electrode further comprises another material comprising vanadium oxides $Li_yVO_x$ wherein ($2x-5 \leq y \leq 2x-3$; $2.15 \leq x \leq 2.5$) manganese spinels $Li_yMn_{2-x}M_xO_4$ wherein M is Li, Cr, Al, V, Ni, $0 \leq x \leq 0.5$ and $0 \leq y \leq 2$, organic polydisulfides, polyquinones, FeS, FeS$_2$, iron sulphate, phosphates and phosphosilicates of iron and lithium of the olivine or Nasicon-type structure, or substitution products of iron with manganese, used alone or in combination.

6. A system according to claim 2 wherein the material further comprises a plasticizer comprising a polar liquid selected from the group consisting of acyclic and cyclic carbonates, γ-butyrolactone, carboxylic acid esters, tetraalkylsulfamides, dialkylated ethers of mono, di, tri and tetraethylene glycols and oligomers of a weight lower than 2000 g/mol and mixtures thereof.

7. A system according to claim 5, wherein the polyquinones comprise rhodizonates.

* * * * *